US008084046B2

(12) United States Patent
Syverson et al.

(10) Patent No.: US 8,084,046 B2
(45) Date of Patent: Dec. 27, 2011

(54) INHIBITION OF EXOPROTEIN PRODUCTION IN ABSORBENT ARTICLES USING ISOPRENOIDS

(75) Inventors: Rae E. Syverson, Fond du Lac, WI (US); Richard A. Proctor, Madison, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1362 days.

(21) Appl. No.: 09/969,199

(22) Filed: Oct. 2, 2001

(65) Prior Publication Data

US 2003/0105439 A1 Jun. 5, 2003

(51) Int. Cl.
*A61K 9/00* (2006.01)

(52) U.S. Cl. .......................................................... 424/400

(58) Field of Classification Search .................. 424/400, 424/422, 443, 430, 431
See application file for complete search history.

(56) References Cited

U.S. PATENT DOCUMENTS

| | | | | |
|---|---|---|---|---|
| 3,796,219 | A * | 3/1974 | Hanke | 604/48 |
| 3,902,493 | A * | 9/1975 | Baier et al. | 604/286 |
| 4,405,323 | A | 9/1983 | Auerbach | |
| 4,413,032 | A | 11/1983 | Hartmann et al. | |
| 4,413,986 | A | 11/1983 | Jacobs | |
| 4,424,054 | A | 1/1984 | Conn et al. | |
| 4,431,427 | A | 2/1984 | Lefren et al. | |
| 4,543,098 | A * | 9/1985 | Wolfe et al. | 604/370 |
| 4,585,792 | A | 4/1986 | Jacob et al. | |
| 4,722,936 | A | 2/1988 | Jacob | |
| 4,722,937 | A | 2/1988 | Jacob et al. | |
| 4,769,021 | A | 9/1988 | Kass | |
| 4,952,211 | A | 8/1990 | Snider | |
| 5,000,749 | A | 3/1991 | LeVeen et al. | |
| 5,070,889 | A | 12/1991 | Leveen et al. | |
| 5,071,648 | A | 12/1991 | Rosenblatt | |
| 5,156,164 | A | 10/1992 | Leveen et al. | |
| 5,221,693 | A | 6/1993 | Shetty | |
| 5,306,706 | A * | 4/1994 | Baydar et al. | 512/2 |
| 5,342,331 | A | 8/1994 | Silber et al. | |
| 5,357,636 | A * | 10/1994 | Dresdner et al. | 2/161.7 |
| 5,364,879 | A * | 11/1994 | Herman | 514/452 |
| 5,389,374 | A * | 2/1995 | Brown-Skrobot | 424/431 |
| 5,476,455 | A | 12/1995 | Silber | |
| 5,498,252 | A | 3/1996 | Silber | |
| 5,527,892 | A | 6/1996 | Borsotti et al. | |
| 5,533,990 | A * | 7/1996 | Yeo | 604/363 |
| 5,540,979 | A | 7/1996 | Yahiaoui et al. | |
| 5,547,985 | A | 8/1996 | Brown-Skrobot et al. | |
| 5,601,814 | A | 2/1997 | Barton et al. | |
| 5,612,045 | A | 3/1997 | Syverson | |
| 5,618,554 | A | 4/1997 | Syverson | |
| 5,641,503 | A | 6/1997 | Brown-Skrobot | |
| 5,661,170 | A | 8/1997 | Chodosh | |
| 5,679,369 | A | 10/1997 | Brown-Skrobot | |
| 5,685,872 | A | 11/1997 | Syverson | |
| 5,705,182 | A | 1/1998 | Brown-Skrobot | |
| 5,719,113 | A | 2/1998 | Fendler et al. | |
| 5,733,272 | A * | 3/1998 | Brunner et al. | 604/359 |
| 5,753,252 | A | 5/1998 | Brown-Skrobot | |
| 5,753,257 | A | 5/1998 | DiPippo et al. | |
| 5,770,543 | A | 6/1998 | Garst et al. | |
| 5,814,567 | A | 9/1998 | Yahiaoui et al. | |
| 5,817,047 | A | 10/1998 | Osborn, III et al. | |
| 5,834,413 | A * | 11/1998 | Durbut et al. | 510/365 |
| 5,932,495 | A | 8/1999 | Boney et al. | |
| 5,945,175 | A | 8/1999 | Yahiaoui et al. | |
| 6,017,832 | A | 1/2000 | Yahiaoui et al. | |
| 6,028,016 | A | 2/2000 | Yahiaoui et al. | |
| 6,039,716 | A | 3/2000 | Jessup et al. | |
| 6,060,636 | A | 5/2000 | Yahiaoui et al. | |
| 6,107,268 | A | 8/2000 | Yahiaoui et al. | |
| 6,159,924 | A | 12/2000 | Weller et al. | |
| 6,224,886 | B1 | 5/2001 | Charlton et al. | |
| 6,231,557 | B1 | 5/2001 | Krautkramer et al. | |
| 6,361,787 | B1 | 3/2002 | Shaheen et al. | |
| 6,506,958 | B2 * | 1/2003 | Williams | 604/361 |
| 6,534,548 | B1 | 3/2003 | Syverson et al. | |
| 6,664,309 | B2 * | 12/2003 | Svenningsen et al. | 523/122 |
| 6,689,767 | B2 * | 2/2004 | Krasutsky et al. | 514/169 |
| 7,402,722 | B2 | 7/2008 | Hill et al. | |
| 7,456,207 | B2 | 11/2008 | Bentley et al. | |
| 7,527,614 | B2 | 5/2009 | Heuer et al. | |
| 2001/0028126 | A1 * | 10/2001 | Williams et al. | 264/103 |

FOREIGN PATENT DOCUMENTS

| | | | |
|---|---|---|---|
| DE | 295 21 478 | U1 | 8/1997 |
| EP | 0 009 977 | A1 | 4/1980 |
| EP | 0 053 221 | A2 | 6/1982 |
| EP | 0 110 793 | B1 | 6/1984 |
| EP | 0 391 741 | A2 | 10/1990 |
| EP | 0 395 099 | A2 | 10/1990 |
| EP | 0 483 812 | B1 | 5/1992 |
| EP | 0 483 835 | A1 | 5/1992 |
| EP | 0 683 260 | A2 | 2/1995 |
| FR | 2 747 310 | A1 | 10/1997 |

(Continued)

OTHER PUBLICATIONS

CAS Registry file for limonene, copyright 2010, accessed Dec. 10, 2010.*

CAS Registry file for alpha-myrcene, copyright 2010, accessed Dec. 10, 2010.*

"Bactericide," http://www.merriam-webster.com/dictionary/bactericide, printed Feb. 3, 2009.

"Bactericide," http://en.wikipedia.org/wiki/Bactericide, printed Feb. 3, 2009; last modified Jan. 9, 2009.

(Continued)

*Primary Examiner* — Michael G Hartley
*Assistant Examiner* — Nissa Westerberg
(74) *Attorney, Agent, or Firm* — Armstrong Teasdale LLP

(57) ABSTRACT

Absorbent articles, such as catamenial tampons, are disclosed. The absorbent articles include an effective amount of an isoprenoid inhibitory compound to substantially inhibit the production of exotoxins by Gram positive bacteria. The isoprenoid inhibitory compounds of the present invention include terpenes and terpenoids which substantially reduce the production of exotoxins by Gram positive bacteria.

92 Claims, No Drawings

FOREIGN PATENT DOCUMENTS

| | | | |
|---|---|---|---|
| GB | 1068667 | | 5/1967 |
| WO | WO 87/03208 | A1 | 6/1987 |
| WO | WO 94/22501 | A1 | 10/1994 |
| WO | WO 96/40300 | A2 | 12/1996 |
| WO | WO 98/09662 | A1 | 3/1998 |
| WO | WO 98/41179 | A1 | 9/1998 |
| WO | WO 99/12505 | A2 | 3/1999 |
| WO | WO 99/61079 | A1 | 12/1999 |

OTHER PUBLICATIONS

Berry, Christine, "Women's Natural Health—The Natural Treatment of Vaginal Infections," http://www.risingwomen.com/arcberry1.htm.

Jakobbson, Tell, "Lactobacillus iners: A Marker of Changes in the Vaginal Flora," http://www.pubmedcentral.nih.gov/articleender.fcgi?artid=2045263.

Print-out of http://www.merriam-webster.com/dictionary/imbalance, last viewed Mar. 25, 2010.

Matsumura et al., Surface Activities, Biodegradability and Antimicrobial Properties of n-Alkyl Glucosides, Mannosides and Galactosides, *J. Amer. Oil Chem. Soc.*, Dec. 1990, pp. 996-1000, vol. 67.

PCT/US02/28758 PCT International Search Report completed Dec. 17, 2002.

* cited by examiner

INHIBITION OF EXOPROTEIN PRODUCTION IN ABSORBENT ARTICLES USING ISOPRENOIDS

BACKGROUND OF THE INVENTION

The present invention relates to the inhibition of exoprotein production in association with an absorbent article such as a catamenial tampon. More particularly, the present invention relates to the incorporation of certain isoprenoid compounds into absorbent articles and the effects of these compounds on Gram positive bacteria.

Disposable absorbent devices, such as catamenial tampons, for the absorption of human exudates are widely used. These disposable devices typically have a compressed mass of absorbent formed into the desired shape, which is typically dictated by the intended consumer use. In the area of a menstrual tampon, the device is intended to be inserted in a body cavity for absorption of the body fluids generally discharged during a woman's menstrual period.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal fluid. The bacterial flora of the vagina is comprised of both aerobic and anaerobic bacteria. The more commonly isolated bacteria are *Lactobacillus* species, *Corynebacteria, Gardnerella vaginalis, Staphylococcus* species, *Peptococcus* species, aerobic and anaerobic *Streptococcus* species, and *Bacteroides* species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (*Herpes simplex*). These latter organisms are generally associated with vaginitis or venereal disease, although they may be present in low numbers without causing symptoms.

Physiological, social, and idiosyncratic factors effect the quantity and species of bacteria present in the vagina. Physiological factors include age, day of the menstrual cycle, and pregnancy. For example, vaginal flora present in the vagina throughout the menstrual cycle can include lactobacilli, corynebacterium, ureaplasma, and mycoplasma. Social and idiosyncratic factors include method of birth control, sexual practices, systemic disease (e.g., diabetes), and medications.

Bacterial proteins and metabolic products produced in the vagina can effect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of lactobacilli and their production of acidic products. Microorganisms in the vagina can also produce antimicrobial compounds such as hydrogen peroxide and bactericides directed at other bacterial species. One example is the lactocins, bacteriocin-like products of lactobacilli directed against other species of lactobacilli.

Some microbial products produced in the vagina may negatively affect the human host. For example, *S. aureus* can produce and excrete into its environment a variety of exoproteins including enterotoxins, Toxic Shock Syndrome Toxin-1 (TSST-1), and enzymes such as proteases and lipase. When absorbed into the bloodstream of the host, TSST-1 may produce Toxic Shock Syndrome (TSS) in non-immune humans.

*S. aureus* is found in the vagina of approximately 16% of healthy women of menstrual age. Approximately 25% of the *S. aureus* isolated from the vagina are found to produce TSST-1. TSST-1 and some of the staphylococcal enterotoxins have been identified as causing TSS in humans.

Symptoms of Toxic Shock Syndrome generally include fever, diarrhea, vomiting and a rash followed by a rapid drop in blood pressure. Multiple organ failure occurs in approximately 6% of those who contract the disease. *S. aureus* does not initiate Toxic Shock Syndrome as a result of the invasion of the microorganism into the vaginal cavity. Instead as *S. aureus* grows and multiplies, it can produce TSST-1. Only after entering the bloodstream does TSST-1 toxin act systemically and produce the symptoms attributed to Toxic Shock Syndrome.

Menstrual fluid has a pH of about 7.3. During menses, the pH of the vagina moves toward neutral and can become slightly alkaline. This change permits microorganisms whose growth is inhibited by an acidic environment the opportunity to proliferate. For example, *S. aureus* is more frequently isolated from vaginal swabs during menstruation than from swabs collected between menstrual periods.

When *S. aureus* is present in an area of the human body that harbors a normal microbial population such as the vagina, it may be difficult to eradicate the *S. aureus* bacterium without harming members of the normal microbial flora required for a healthy vagina. Typically, antibiotics that kill *S. aureus* are not an option for use in catamenial products because of their effect on the normal vaginal microbial flora and their propensity to stimulate toxin production if all of the *S. aureus* are not killed. An alternative to eradication is technology designed to prevent or substantially reduce the bacterium's ability to produce toxins.

There have been numerous attempts to reduce or eliminate pathogenic microorganisms and menstrually occurring Toxic Shock Syndrome by incorporating into a tampon pledget one or more biostatic, biocidal, and/or detoxifying compounds. For example, L-ascorbic acid has been applied to a menstrual tampon to detoxify toxin found in the vagina. Others have incorporated monoesters and diesters of polyhydric aliphatic alcohols, such as glycerol monolaurate, as biocidal compounds (see, e.g., U.S. Pat. No. 5,679,369). Still others have introduced other non-ionic surfactants, such as alkyl ethers, alkyl amines, and alkyl amides as detoxifying compounds (see, e.g., U.S. Pat. Nos. 5,685,872, 5,618,554, and 5,612, 045).

Despite the aforementioned art, there continues to be a need for compounds that will effectively inhibit the production of exoproteins, such as TSST-1, from Gram positive bacteria, maintain activity even in the presence of the enzymes lipase and esterase which can have adverse effects on potency and which may also be present in the vagina. Further, it is desirable that the detoxifying compounds useful in the inhibition of the production of exoproteins be substantially non-harmful to the natural flora found in the vaginal area.

SUMMARY OF THE INVENTION

The present invention is based on the discovery that when one or more isoprenoid compounds, such as a terpene compound or terpenoid compound, are incorporated into an absorbent article, such as a catamenial tampon, the production of exoprotein in Gram positive bacterium is substantially inhibited.

It is a general object of the present invention to provide an absorbent article which inhibits the production of exoprotein from Gram positive bacterium. A more specific object of the present invention is to provide a catamenial tampon incorporating one or more isoprenoid compounds which act to substantially inhibit the production of TSST-1 and Enterotoxin B by *S. aureus.*

Another object of the present invention is to provide a catamenial tampon incorporating one or more isoprenoid compounds in combination with one or more other inhibitory ingredients such as, but not limited to, for example, laureth-4, PPG-5 lauryl ether, 1-0-dodecyl-rac-glycerol, disodium laureth sulfosuccinate, glycerol monolaurate, alkylpolyglycosides, polyethylene oxide (2) sorbital ether or myreth-3-myristate which in combination act to substantially inhibit the production of TSST-1, alpha hemolysin, and Enterotoxin B by *S. aureus.*

A further object of the present invention is to provide a catamenial tampon that has incorporated therewith one or more isoprenoid compounds that will inhibit the production of exoproteins from Gram positive bacterium without significantly imbalancing the natural flora present in the vaginal tract.

Other objects and advantages of the present invention, and modifications thereof, will become apparent to persons skilled in the art without departure from the inventive concepts defined in the claims.

DETAILED DESCRIPTION OF THE PREFERRED EMBODIMENTS

In accordance with the present invention, it has been discovered that isoprenoid compounds as described herein can be used in combination with an absorbent article, such as a catamenial tampon, to substantially inhibit the production of exoproteins, such as TSST-1, from Gram positive bacteria without substantially imbalancing the natural flora present in the vaginal tract. It has also been discovered that the isoprenoid compounds can also be used in combination with other surface-active agents such as, for example, compounds with an ether, ester, amide, glycosidic, or amine bond linking a $C_8$-$C_{18}$ fatty acid to an aliphatic alcohol, polyalkoxylated sulfate salt, or polyalkoxylated sulfosuccinic salt, to substantially inhibit the production of exoproteins such as TSST-1 from Gram positive bacteria without substantially imbalancing the natural flora present in the vaginal tract.

This invention will be described herein in detail in connection with a catamenial tampon, but will be understood by persons skilled in the art to be applicable to other disposable absorbent articles such as sanitary napkins, panty liners, adult incontinence garments, diapers, medical bandages and tampons such as those intended for medical, dental, surgical, and/or nasal use wherein the inhibition of exoproteins from Gram positive bacteria would be beneficial. As used herein, the phrase "absorbent article" generally refers to devices which absorb and contain body fluids, and more specifically, refers to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to, health care related products including bandages and tampons such as those intended for medical, dental, surgical and/or nasal use; personal care absorbent products such as feminine hygiene products (e.g., sanitary napkins, panty liners, and catamenial tampons), diapers, training pants, incontinent products and the like, wherein the inhibition of the production of exoproteins from Gram positive bacteria would be beneficial.

Catamenial tampons suitable for use with the present invention are typically made of absorbent fibers, including natural and synthetic fibers, compressed into a unitary body of a size which may easily be inserted into the vaginal cavity. Suitable fibers include, for example, cellulosic fibers such as cotton and rayon. Fibers may be 100% cotton, 100% rayon, a blend of cotton and rayon, or other materials known to be suitable for tampon use.

Catamenial tampons are typically made in an elongated cylindrical form in order that they may have a sufficiently large body of material to provide the required absorbing capacity, but may be made in a variety of shapes. The tampon may or may not be compressed, although compressed types are now generally preferred. The tampon may be made of various fiber blends including both absorbent and nonabsorbent fibers, which may or may not have a suitable cover or wrapper. Suitable methods and materials for the production of tampons are well known to those skilled in the art.

It has been discovered that certain isoprenoid compounds can substantially inhibit the production of exoprotein by Gram positive bacterium and, specifically, the production of TSST-1, alpha hemolysin, and Enterotoxin B from *S. aureus* bacterium. As used herein, the term "isoprenoid compound" means a hydrocarbon containing compound structurally based on multiple isoprene units which may or may not be substituted and may or may not contain hetero atoms and functional groups such as carbonyls, ketones, aldehydes, and alcohols. Isoprene, also commonly referred to as 2-methyl-1,3-butadiene, has the following chemical structure:

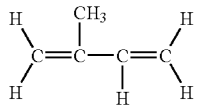

Desirably, the isoprenoid compounds used in the accordance with the present invention are terpenes. As used herein, "terpene compound" refers to compounds which are based on isoprene, but which may contain heteroatoms such as oxygen and/or alcohols, aldehydes, ketones and/or carbonyls.

Various types and kinds of terpenes are useful in accordance with the present invention. Suitable terpenes include hemiterpenes (terpenes containing 5 carbon atoms), monoterpenes (terpenes containing 10 carbon atoms), sesquiterpenses (terpenes containing 15 carbon atoms), diterpenes (terpenes containing 20 carbon atoms), triterpenes (terpenes containing 30 carbon atoms), tetraterpenes (terpenes containing 40 carbon atoms), as well as polyterpenes and mixtures and combinations thereof. Terpenoids, oxygenated derivatives of terpenes which may or may not contain hydroxyl and/or carbonyl groups, are also useful in the present invention and can be used in combination with the terpenes described above.

The terpenes, terpenoids and derivatives described herein and useful in the present invention, may be cyclic or acyclic, and may be saturated or unsaturated. Examples of monoterpenes useful in the present invention include, for example, α-pinen, β-pinen, campher, geraniol, borneol, nerol, thujone, citral a, limonen, cineole, terpineol, terpinene, terpin (cis and trans), α-myrcene, β-myrcene, dipentene, linalool, 2-methyl-6-methylene-1,7-octadiene, and menthol. Examples of sesquiterpenes useful in the present invention include, for example, humulene, ionone, nerolidol and farnesol. An example of a suitable diterpene is phytol. A suitable triterpene for use in the present invention is squalen. Suitable tetraterpenes for use in the present invention include α-carotene, β-carotene, γcarotene, δ-carotene, lutein, and violaxanthin.

Preferred isoprenoid compounds of the present invention include terpineol, β-ionone, terpin (cis and trans), linalool, geraniol, and menthol, and mixtures and combinations thereof.

In accordance with the present invention, the absorbent article including the isoprenoid compound contains an effective amount of the inhibiting isoprenoid compound to substantially inhibit the formation of TSST-1 when the absorbent article is exposed to *S. aureus* bacteria. Several methods are known in the art for testing the effectiveness of potential inhibitory agents on the inhibition of the production of TSST-1 by *S. aureus*. One such preferred method is set forth in Example 1 shown below. When tested in accordance with the testing methodology set forth herein, preferably, the inhibiting isoprenoid compounds reduce the formation of TSST-1 when the absorbent article is exposed to *S. aureus* by at least about 40%, more preferably by at least about 50%, still more preferably by at least about 60%, still more preferably by at least about 70%, still more preferably by at least about 80%, still more preferably by at least about 90%, and still more preferably by at least about 95%.

Effective amounts of isoprenoid compound that significantly reduce the production of TSST-1 have been found to be at least about 0.1 micromoles of the isoprenoid compound per gram of the absorbent product. Preferably, the isoprenoid compound ranges from about 0.5 micromoles per gram of absorbent to about 100 micromoles per gram of absorbent and more preferably from about 1 micromole per gram of absorbent to about 50 micromoles per gram of absorbent. Although "isoprenoid compound" is used in the singular, one skilled in the art would understand that it includes the plural, and that various isoprenoid compounds within the scope of this invention may be used in combination.

The isoprenoid compounds of the present invention can be prepared and applied in any suitable form, but are preferably prepared in forms including, without limitation, aqueous solutions, lotions, balms, gels, salves, ointments, boluses, liposomes, suppositories, and the like.

The isoprenoid compounds may be applied to the absorbent article using conventional methods for applying an inhibitory agent to the desired absorbent article. For example, unitary tampons without separate wrappers may be dipped directly into a liquid bath having the inhibitory compound and then can be air dried, if necessary, to remove any volatile solvents. For compressed tampons, impregnating any of its elements is best done before compressing. The isoprenoid compounds when incorporated on and/or into the tampon materials may be fugitive, loosely adhered, bound, or any combination thereof. As used herein, the term "fugitive" means that the composition is capable of migrating through the tampon materials.

It is not necessary to impregnate the entire absorbent body of the tampon with the inhibitory isoprenoid compound. Optimum results both economically and functionally can be obtained by concentrating the material on or near the outer surface where it may be most effective during use.

The substantially inhibitory isoprenoid compounds may additionally employ one or more conventional pharmaceutically-acceptable and compatible carrier materials useful for the desired application. The carrier can be capable of co-dissolving or suspending the materials used in the absorbent article. Carrier materials suitable for use in the instant invention include those well-known for use in the cosmetic and medical arts as a basis for ointments, lotions, creams, salves, aerosols, suppositories, gels, and the like.

The isoprenoid compounds of the present invention may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

In another embodiment of the present invention, the inhibitory isoprenoid compounds described above can be used in combination with one or more surface active agents to reduce the production of TSST-1 without significantly eliminating the beneficial bacterial flora. The surface active agents can include, for example, compounds with an ether, ester, amide, glycosidic, or amine bond linking a $C_8$-$C_{18}$ fatty acid to an aliphatic alcohol, polyalkoxylated sulfate salt, or polyalkoxylated sulfosuccinic salt.

In one embodiment, the inhibitory isoprenoid compounds described herein can be used in combination with ether compounds having the general formula:

$$R^{10}—O—R^{11}$$

wherein $R^{10}$ is a straight or branched alkyl or alkenyl group having a chain of from about 8 to about 18 carbon atoms and $R^{11}$ is selected from an alcohol, a polyalkoxylated sulfate salt or a polyalkoxylated sulfosuccinate salt.

The alkyl, or the $R^{10}$ moiety of the ether compounds useful for use in combination with the inhibitory aromatic compounds described herein, can be obtained from saturated and unsaturated fatty acid compounds. Suitable compounds include, $C_8$-$C_{18}$ fatty acids, and preferably, fatty acids include, without limitation, caprylic, capric, lauric, myristic, palmitic and stearic acid whose carbon chain lengths are 8, 10, 12, 14, 16, and 18, respectively. Highly preferred materials include capric, lauric, and myristic acids.

Preferred unsaturated fatty acids are those having one or two cis-type double bonds and mixtures of these materials. Suitable materials include myrystoleic, palmitoleic, linolenic and mixtures thereof.

Desirably, the $R^{11}$ moiety is an aliphatic alcohol which can be ethoxylated or propoxylated for use in the ether compositions in combination with the inhibitory aromatic compounds described herein. Suitable aliphatic alcohols include glycerol, sucrose, glucose, sorbitol and sorbitan. Preferred ethoxylated and propoxylated alcohols include glycols such as ethylene glycol, propylene glycol, polyethylene glycol and polypropylene glycol.

The aliphatic alcohols can be ethoxylated or propoxylated by conventional ethoxylating or propoxylating compounds and techniques. The compounds are preferably selected from the group consisting of ethylene oxide, propylene oxide, and mixtures thereof, and similar ringed compounds which provide a material which is effective.

The $R^{11}$ moiety can further include polyalkoxylated sulfate and polyalkoxylated sulfosuccinate salts. The salts can have one or more cations. Preferably, the cations are sodium, potassium or both.

Preferred ether compounds for use in combination with the inhibitory isoprenoid compounds described herein include laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate, and polyethylene oxide (2) sorbitol ether.

In accordance with the present invention, the absorbent article contains an effective amount of the combination of the inhibitory isoprenoid and ether 5 compounds. The amount of ether compound included in the absorbent article is at least about 0.0001 millimoles of ether compound per gram of absorbent article, and preferably at least about 0.005 millimoles of ether compound per gram of absorbent article. In a preferred embodiment, the absorbent article contains from about 0.005 millimoles of ether compound per gram of absorbent article to about 2 millimoles of ether compound per gram of absorbent article.

The absorbent articles of the present invention containing a combination of two active ingredients can be a variety of absorbent articles including, for example, catamenial tampons, sanitary napkins, panty liners, incontinent undergarments, diapers, wound dressings, dental tampons, medical tampons, surgical tampons, nasal tampons and the like.

The absorbent articles of the present invention containing a first inhibitory isoprenoid compound and a second inhibitory ether compound contain a sufficient amount of both inhibitory compounds to substantially inhibit the formation of TSST-1 when the absorbent article is exposed to *S. aureus* bacteria. Preferably, the combination of inhibitory compounds reduces the formation of TSST-1 when the absorbent article is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

The absorbent articles of the present invention containing the combination of isoprenoid inhibitory compounds and ether inhibitory compounds may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

Typically, the absorbent article will contain a molar ratio of inhibitory isoprenoid compound to ether compound of from about 1:0.1 to about 1:20.

In another embodiment, the inhibitory isoprenoid compounds described herein can be used in combination with an alkyl polyglycoside compound. Suitable alkyl polyglycosides for use in combination with the inhibitory isoprenoid compounds include alkyl polyglycosides having the general formula:

$$H—(Z_n)—O—R^{14}$$

wherein Z is a saccharide residue having 5 or 6 carbon atoms, n is a whole number from 1 to 6, and $R^{14}$ is a linear or branched alkyl group having from about 8 to about 18 carbon atoms. Commercially available examples of suitable alkyl polyglycosides having differing carbon chain lengths include Glucopon 220, 225, 425, 600, and 625, all available from Henkel Corporation (Ambler, Pa.). These products are all mixtures of alkyl mono- and oligoglucopyranosides with differing alkyl group chain lengths based on fatty alcohols derived from coconut and/or palm kernel oil. Glucopon 220, 225, and 425 are examples of particularly suitable alkyl polyglycosides for use in combination with the inhibitory aromatic compounds of the present invention. Another example of a suitable commercially available alkyl polyglycoside is TL 2141, a Glucopon 220 analog available from ICI Surfactants (Wilmington, Del.).

It should be understood that as referred to herein, an alkylpolyglycoside may consist of a single type of alkyl polyglycoside molecule or, as is typically the case, may include a mixture of different alkyl polyglycoside molecules. The different alkyl polyglycoside molecules may be isomeric and/or may be alkyl polyglycoside molecules with differing alkyl group and/or saccharide portions. By use of the term alkyl poyglycoside isomers reference is made to alkyl polyglycosides which, although including the same alky ether residues, may vary with respect to the location of the alkyl ether residue in the alkyl polyglycoside as well as isomers which differ with respect to the orientation of the functional groups about one or more chiral centers in the molecules. For example, an alkyl polyglycoside can include a mixture of molecules with saccharide portions which are mono, di-, or oligosaccharides derived from more than one 6 carbon saccharide residue and where the mono-, di- or oligosaccharide has been etherified by reaction with a mixture of fatty alcohols of varying carbon chain length. The present alkyl polyglycosides desirably include alkyl groups where the average number of carbon atoms in the alkyl chain is about 8 to about 12. One example of a suitable alkyl polyglycoside is a mixture of alkyl polyglycoside molecules with alkyl chains having from about 8 to about 10 carbon atoms.

The alkyl polyglycosides employed in the absorbent articles in combination with the inhibiting isoprenoid compounds can be characterized in terms of their hydrophilic lipophilic balance (HLB). This can be calculated based on their chemical structure using techniques well known to those skilled in the art. The HLB of the alkyl polyglycosides used in the present invention typically falls within the range of about 10 to about 15. Desirably, the present alkyl polyglycosides have an HLB of at least about 12 and, more desirably, about 12 to about 14.

In accordance with the present invention, the absorbent article contains an effective amount of the combination of the inhibitory isoprenoid and alkyl polyglycoside compounds. The amount of alkyl polyglycoside compound included in the absorbent article is at least about 0.0001 millimoles of alkyl polyglycoside per gram of absorbent article, and preferably at least about 0.005 millimoles of alkyl polyglycoside per gram of absorbent article. In a preferred embodiment, the absorbent article contains from about 0.005 millimoles per gram of absorbent article to about 2 millimoles per gram of absorbent article.

The absorbent articles of the present invention containing a combination of inhibitory or active ingredients such as isoprenoid inhibitory compounds and alkyl polyglycoside inhibitory compounds can be a variety of absorbent articles including, for example, catamenial tampons, sanitary napkins, panty liners, incontinent undergarments, diapers, wound dressings, dental tampons, medical tampons, surgical tampons, nasal tampons and the like.

The absorbent articles of the present invention containing a first inhibitory isoprenoid compound and a second inhibitory alkyl polyglycoside compound contain a sufficient amount of both inhibitory compounds to substantially inhibit the formation of TSST-1 when the absorbent article is exposed to *S. aureus* bacteria. Preferably, the combination of inhibitory compounds reduces the formation of TSST-1 when the absorbent article is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

The absorbent articles of the present invention containing the combination of isoprenoid inhibitory compounds and alkyl polyglycoside inhibitory compounds may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

Typically, the absorbent article will contain a molar ratio of inhibitory isoprenoid compound to alkyl glycoside compound of from about 1:1 to about 1:0.05.

In another embodiment, the inhibitory isoprenoid compounds described herein can be used in combination with an amide containing compound having the general formula:

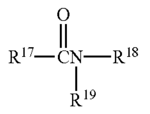

wherein $R^{17}$, inclusive of the carbonyl carbon, is an alkyl group having 8 to 18 carbon atoms, and $R^{18}$ and $R^{19}$ are independently selected from hydrogen or an alkyl group having from 1 to about 12 carbon atoms which may or may not be substituted with groups selected from ester groups, ether groups, amine groups, hydroxyl groups, carboxyl groups, carboxyl salts, sulfonate groups, sulfonate salts, and mixtures thereof.

$R^{17}$ can be derived from saturated and unsaturated fatty acid compounds. Suitable compounds include, $C_8$-$C_{18}$ fatty acids, and preferably, the fatty acids include, without limitation, caprylic, capric, lauric, myristic, palmitic and stearic acid whose carbon chain lengths are 8, 10, 12, 14, 16, and 18, respectively. Highly preferred materials include capric, lauric, and myristic.

Preferred unsaturated fatty acids are those having one or two cis-type double bonds and mixtures of these materials. Suitable materials include myrystoleic, palmitoleic, linolenic and mixtures thereof.

The $R^{18}$ and $R^{19}$ moieties can be the same or different and each being selected from hydrogen and an alkyl group having a carbon chain having from 1 to about 12 carbon atoms. The $R^{18}$ and $R^{19}$ alkyl groups can be straight or branched and can be saturated or unsaturated. When $R^{18}$ and/or $R^{19}$ are an alkyl moiety having a carbon chain of at least 2 carbons, the alkyl group can include one or more substituent groups selected from ester, ether, amine, hydroxyl, carboxyl, carboxyl salts, sulfonate and sulfonate salts. The salts can have one or more cations selected from sodium, potassium or both.

Preferred amide compounds for use in combination with the inhibitory isoprenoid compounds described herein include sodium lauryl sarcosinate, lauramide monoethanolamide, lauramide diethanolamide, lauramidopropyl dimethylamine, disodium lauramido monoethanolamide sulfosuccinate and disodium lauroamphodiacetate.

In accordance with the present invention, the absorbent article contains an effective amount of the combination of the inhibitory isoprenoid and amide-containing compounds. The amount of amide-containing compound included in the absorbent article is at least about 0.0001 millimoles of nitrogen containing compound per gram of absorbent article, and preferably at least about 0.005 millimoles of nitrogen containing compound per gram of absorbent article. In a preferred embodiment, the absorbent article contains from about 0.005 millimoles per gram of absorbent article to about 2 millimoles per gram of absorbent article.

The absorbent articles of the present invention containing a combination of inhibitory or active ingredients such as isoprenoid inhibitory compounds and amide-containing inhibitory compounds can be a variety of absorbent articles including, for example, catamenial tampons, sanitary napkins, panty liners, incontinent undergarments, diapers, wound dressings, dental tampons, medical tampons, surgical tampons, nasal tampons and the like.

The absorbent articles of the present invention containing a first inhibitory isoprenoid compound and a second inhibitory amide-containing compound contain a sufficient amount of both inhibitory compounds to substantially inhibit the formation of TSST-1 when the absorbent article is exposed to *S. aureus* bacteria. Preferably, the combination of inhibitory compounds reduces the formation of TSST-1 when the absorbent article is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

The absorbent articles of the present invention containing the combination of isoprenoid inhibitory compounds and amide-containing inhibitory compounds may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

Typically, the absorbent article will contain a molar ratio of inhibitory isoprenoid compound to amide-containing compound of from about 1:2 to about 1:0.01.

In another embodiment, the inhibitory compounds described herein can be used in combination with amine compounds having the general formula:

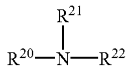

wherein $R^{20}$ is an alkyl group having from about 8 to about 18 carbon atoms and $R^{21}$ and $R^{22}$ are independently selected from the group consisting of hydrogen and alkyl groups having from 1 to about 18 carbon atoms and which can have one or more substitutional moieties selected from the group consisting of hydroxyl, carboxyl, carboxyl salts and imidazoline. The combination of aromatic compounds and amine compounds are effective in substantially inhibiting the production of exoprotein from Gram positive bacteria.

Desirably, $R^{20}$ is derived from fatty acid compounds which include, without limitation, caprylic, capric, lauric, myristic, palmitic and stearic acid whose carbon chain lengths are 8, 10, 12, 14, 16, and 18, respectively. Highly preferred materials include capric, lauric, and myristic. Preferred unsaturated fatty acids are those having one or two cis-type double bonds and mixtures of these materials. Suitable materials include myrystoleic, palmitoleic, linolenic, and mixtures thereof.

The $R^{21}$ and $R^{22}$ alkyl groups can further include one or more substitutional moieties selected from hydroxyl, carboxyl, carboxyl salts, and $R^1$ and $R^2$ can form an unsaturated heterocyclic ring that contains a nitrogen that connects via a double bond to the alpha carbon of the $R^1$ moiety to form a substituted imidazoline. The carboxyl salts can have one or more cations selected from sodium potassium or both. The $R^{20}$, $R^{21}$, and $R^{22}$ alkyl groups can be straight or branched and can be saturated or unsaturated.

Preferred amine compounds for use with the isoprenoid compounds described herein include triethanolamide laureth sulfate, lauramine, lauramino propionic acid, sodium lauriminodipropionic acid, lauryl hydroxyethyl imidazonline and mixtures thereof.

In another embodiment, the amine compound can be an amine salt having the general formula:

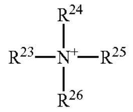

wherein $R^{23}$ is an anionic moiety associated with the amine and is derived from an alkyl group having from about 8 to about 18 carbon atoms, and $R^{24}$, $R^{25}$, and $R^{26}$ are independently selected from the group consisting of hydrogen and alkyl group having from 1 to about 18 carbon atoms and which can have one or more substitutional moieties selected from the group consisting of hydroxyl, carboxyl, carboxyl salts, and imidazoline. $R^{24}$, $R^{25}$, and $R^{26}$ can be saturated or unsaturated. Desirably, $R^{23}$ is a polyalkyloxylated alkyl sulfate. A preferred compound illustrative of an amine salt is triethanolamide laureth sulfate.

In accordance with the present invention, the absorbent article contains an effective amount of the combination of the inhibitory isoprenoid and amine and/or amine salt compounds. The amount of amine and/or amine salt compound included in the absorbent article is at least about 0.0001 millimoles of ether per gram of absorbent article, and preferably at least about 0.005 millimoles of ether per gram of absorbent article. In a preferred embodiment, the absorbent article contains from about 0.005 millimoles per gram of absorbent article to about 2 millimoles per gram of absorbent article.

The absorbent articles of the present invention containing a combination of two active ingredients can be a variety of absorbent articles including, for example, catamenial tampons, sanitary napkins, panty liners, incontinent undergarments, diapers, wound dressings, dental tampons, medical tampons, surgical tampons, nasal tampons and the like.

The absorbent articles of the present invention containing a first inhibitory isoprenoid compound and a second inhibitory amine and/or amine salt compound contain a sufficient amount of both inhibitory compounds to substantially inhibit the formation of TSST-1 when the absorbent article is exposed to *S. aureus* bacteria. Preferably, the combination of inhibitory compounds reduces the formation of TSST-1 when the absorbent article is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

The absorbent articles of the present invention containing the combination of isoprenoid inhibitory compounds and amine and/or amine salt inhibitory compounds may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

Typically, the absorbent article will contain a molar ratio of inhibitory isoprenoid compound to amine and/or amine salt compound of from about 1:2 to about 1:0.05.

The present invention is illustrated by the following examples which are merely for the purpose of illustration and are not to be regarded as limiting the scope of the invention or manner in which it may be practiced.

EXAMPLE 1

In this Example, the effect of terpineol on the growth of *S. aureus* and the production of TSST-1 was determined. Terpineol, in the desired concentration (expressed in percent of terpineol) was placed in 10 mL of a growth medium in a sterile, 50 mL conical polypropylene tube (Sarstedt, Inc. Newton N.C.).

The growth medium was prepared by dissolving 37 grams of brain heart infusion broth (BHI) (Difco Laboratories, Cockeysville, Md.) in 880 mL of distilled water and sterilizing the broth according to the manufacturer's instructions. The BHI was supplemented with fetal bovine serum (FBS) (100 mL) (Sigma Chemical Company, St. Louis, Mo.). Hexahydrate of magnesium chloride (0.021 M, 10 mL) (Sigma Chemical Company, St. Louis, Mo.) was added to the BHI-FBS mixture. Finally, L-glutamine (0.027 M, 10 mL) (Sigma Chemical Company, St. Louis, Mo.) was added to the mixture.

Terpineol was added directly to the growth medium and diluted in growth medium to obtain the desired final concentrations.

In preparation for inoculation of the tubes of growth medium containing the terpineol, an inoculating broth was prepared as follows: *S. aureus* (MN8) was streaked onto a tryptic soy agar plate (TSA; Difco Laboratories Cockeysville, Md.) and incubated at 35° C. The test organism was obtained from Dr. Pat Schlievert, Department of Microbiology, University of Minnesota Medical School, Minneapolis Minn. After 24 hours of incubation three to five individual colonies were picked with a sterile inoculating loop and used to inoculate 10 mL of growth medium. The tube of inoculated growth medium was incubated at 35° C. in atmospheric air. After 24 hours of incubation, the culture was removed from the incubator and mixed well on a S/P brand vortex mixer. A second tube containing 10 mL of the growth medium was inoculated with 0.5 mL of the above-described 24 hour old culture and incubated at 35° C. in atmospheric air. After 24 hours of incubation the culture was removed from the incubator and mixed well on a S/P brand vortex mixer. The optical density of the culture fluid was determined in a microplate reader (Bio-Tek Instruments, Model EL309, Winooski, Vt.). The amount of inoculum necessary to give $5\times10^6$ CFU/mL in 10 mL of growth medium was determined using a standard curve.

This Example included tubes of growth medium with varying concentrations of terpineol, tubes of growth medium without terpineol, (control) and tubes of growth medium with 20-400 microliters of methanol (control). Each tube was inoculated with the amount of inoculum determined as described above. The tubes were capped with foam plugs (Identi-plug plastic foam plugs, Jaece Industries purchased from VWR Scientific Products, South Plainfield, N.J.). The tubes were incubated at 35° C. in atmospheric air containing 5% by volume $CO_2$. After 24 hours of incubation the tubes were removed from the incubator and the optical density (600 nm) of the culture fluid was determined and the culture fluid was assayed for the number of colony forming units of *S. aureus* and was prepared for the analysis of TSST-1 as described below.

The number of colony forming units per mL after incubation was determined by standard plate count procedures. The culture fluid broth was centrifuged and the supernatant subsequently filter sterilized through an Autovial 5 syringeless filter, 0.2 micrometers pore size (Whatman, Inc., Clifton, N.J.). The resulting fluid was frozen at −70° C. until assayed.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, TSST-1 (#TT-606), rabbit polyclonal anti-TSST-1 IgG (LTI-101), rabbit polyclonal anti-TSST-1 IgF conjugated to horseradish peroxidase (LTC-101), and normal rabbit serum (NRS) certified anti-TSST-1 free (NRS-10) were purchased from Toxin Technology (Sarasota, Fla.). A 10 microgram/millimeter solution of the polyclonal rabbit anti-TSST-1 IgG was prepared in phosphate buffered saline (PBS) (pH=7.4). The PBS was prepared from 0.016 molar $NaH_2PO_4$, 0.004 molar $NaH_2PO_4$—$H_2O$, 0.003 molar KCl and 0.137 molar NaCl, (Sigma Chemical Company, St. Louis, Mo.). One hundred microliters of the polyclonal rabbit anti-TSST-1 IgG solution was pipetted into the inner wells of polystyrene microplates. The plates were covered and incubated at room temperature overnight. Unbound anti-toxin was removed by draining until dry. TSST-1 was diluted to 10 nanograms/milliliter in PBS with phosphate buffered saline (pH=7.4) containing 0.05% (vol/vol) Tween-20 (PBS-Tween) (Sigma Chemical Company, St. Louis, Mo.) and 1% NRS (vol/vol) and incubated at 4° C. overnight. Test samples were combined with 1% NRS (vol/vol) and incubated at 4° C. overnight. The plates were treated with 100 microliters of a 1% solution of the sodium salt of casein in PBS (Sigma Chemical Company, St. Louis, Mo.), covered and incubated at 35° C. for one hour. Unbound BSA was removed by 3 washes with PBS-Tween. TSST-1 reference standard (10 nanograms/milliliter) treated with NRS, test samples treated with NRS, and reagent controls were pipetted in 200 microliter volumes to their respective wells on the first and seventh columns of the plate. One hundred microliters of PBS-Tween was added to the remaining wells. The TSST-1 reference standard and test samples were then serially diluted 6 times in the PBS-Tween by transferring 100 microliters from well-to-well. The samples were mixed prior to transfer by repeated aspiration and expression. Samples of the test samples and the TSST-1 reference standard were assayed in triplicate. This was followed by incubation for 1.5 hours at 35° C. and five washes with PBS-T and three washes with distilled water to remove unbound toxin. The rabbit polyclonal anti-TSST-1 IgG conjugated to horseradish peroxidase wash diluted according to manufacturer's instructions and 50 microliters was added to each microtiter well, except well A-1, the conjugate control well. The plates were covered and incubated at 35° C. for one hour.

Following incubation the plates were washed five times in PBS-Tween and three times with distilled water. Following the washes, the wells were treated with 100 microliters of horseradish peroxidase substrate buffer consisting of 5 milligrams of o-phenylenediamine and 5 microliters of 30% hydrogen peroxide in 11 mL of citrate buffer (pH=5.5). The citrate buffer was prepared from 0.012 anhydrous citric acid and 0.026 molar dibasic sodium phosphate. The plates were incubated for 15 minutes at 35° C. The reaction was stopped by the addition of 50 microliters of a 5% sulfuric acid solution. The intensity of the color reaction in each well was evaluated using the BioTek Model EL309 microplate reader (OD 490 nanometers). TSST-1 concentrations in the test samples were determined from the reference toxin regression equation derived during each assay procedure. The efficacy of the terpineol in inhibiting the production of TSST-1 is shown in Table I below.

In accordance with the present invention, the data in Table I shows that *S. aureus* (MN8), when compared to the control, produced significantly less TSST-1 in the presence of the terpineol. The terpineol reduced the amount of exotoxin production by about 98%. However, although the amount of toxin produced was significantly reduced, there was minimal, if any, effect on the growth of *S. aureus* cells.

TABLE 1

| Compound | % Test Compound | Optical Density | CFU/mL | ng TSST-1 per OD Unit | Reduction of Toxin (%) |
|---|---|---|---|---|---|
| Growth Medium | Zero | 0.625 | 2.8E + 08 | 1504 | N/A |
| Methanol | 400 µL | 0.627 | 2.8E + 08 | 1440 | N/A |
| Terpineol | 0.1% | 0.811 | 4.5E + 08 | 36 | 98% |

N/A = Not Applicable

EXAMPLE 2

In this Example, the effect of menthol on the growth of *S. aureus* and the production of TSST-1 was determined. Menthol (Sigma Chemical Company, St. Louis, Mo.) was dissolved in methanol, spectrophotometric grade, at a concentration that permitted the addition of 200 microliters of the solution to 10 mL of growth medium for the highest concentration tested. The effect of the menthol tested in this Example was determined by placing the desired concentration, expressed in percent of the menthol, in 10 mL of a growth medium as described in Example 1. The test compound was then tested and evaluated as in Example 1.

In accordance with the present invention, Table 2 shows that *S. aureus* (MN8), when compared to the control, produced significantly less TSST-1 in the presence of the menthol. The menthol reduced the amount of exotoxin production by about 97%. However, although the amount of toxin produced was significantly reduced, there was minimal, if any, effect on the growth of *S. aureus* cells.

TABLE 2

| Compound | % Test Compound | Optical Density | CFU/mL | ng TSST-1 per OD Unit | Reduction of Toxin % |
|---|---|---|---|---|---|
| Growth Medium | Zero | 0.606 | 3.2E + 09 | 1445 | N/A |
| Methanol | 100 µL | 0.567 | 1.3E + 09 | 1151 | N/A |
| Menthol | 0.1% | 0.621 | 6.3E + 08 | 33 | 97% |

N/A = Not Applicable

EXAMPLE 3

In this Example, the growth of *S. aureus* and the production of TSST-1 in the presence of various monoterpenes (Sigma Chemical Company) was measured. Test compounds were received as liquids or solids. The liquids were added directly to the growth mdium and diluted in growth medium to obtain the desired final concentrations. The solids were dissolved in methanol, spectrophotometric grade (Sigma Chemical Company) at a concentration that permitted the addition of 200 microliters of the solution to 10 mL of growth medium for the highest concentration tested. Each test compound that was dissolved in methanol was added to the growth medium in the amount required to obtain the desired final concentration. The effect of the monoterpenes was determined by placing the desired concentration, expressed in percent of the monoterpene, in 10 mL of a growth medium prepared as in Example 1. The monoterpenes were then tested and evaluated as in Example 1. Table 3 below shows that *S. aureus*, when compared to the control, produce significantly less TSST-1 in the presence of the monoterpenes. At the concentrations tested, the monoterpenes reduced the amount of toxin produced by 78% to 100%.

TABLE 3

| Compound | % Test Compound | Optical Density | CFU/mL | ng TSST-1 per OD Unit | Reduction of Toxin % |
|---|---|---|---|---|---|
| Methanol | 200 μL | 0.580 | 2.0E + 09 | 3652 | N/A |
| Beta-ionone | 0.8% | 0.688 | 1.8E + 08 | none detected | 100% |
| p-menthane-1,8-diol | 0.7% | 0.620 | 2.0E + 09 | 792 | 78% |
| Linalool | 0.01% | 0.600 | 2.0E + 09 | 421 | 88% |
| Geraniol | 0.01% | 0.0569 | 3.2E + 08 | 26 | 99% |

N/A = Not Applicable

EXAMPLE 4

In this Example, the effect of terpineol on the production of alpha-toxin from *S. aureus* strain RN 6390 was evaluated utilizing a standard hemolytic assay.

The *S. aureus* alpha-toxin is a hemolytic exoprotein that causes target cell membrane damage and cell death. It is produced under environmental conditions similar to those seen with TSST-1 production. The effect of terpineol on the growth and the production of alpha-toxin was carried out by placing the desired concentrations, expressed in percent of the active compound, in 100 mL of growth medium in 500 mL fleakers capped with aluminum foil. The growth medium and inoculum were prepared as described in Example 1. The fleakers were incubated in a 37° C. water bath with a gyratory shaker set at 180 rpm. Growth was followed by periodic optical density measurements at 600 nm. When the growth obtained an optical density of 1.0, 10 mL aliquots were removed for analysis. Plate counts were performed on the samples to determine cell count and culture purity. The remaining sample was centrifuged at 2500 rpm for 15 minutes and the resulting supernatant filter sterilized and frozen at −70° C. until assayed.

Defibrinated rabbit red blood cells (Hema Resources, Aurora, Oreg.) were washed 3 times in Tris-saline buffer and re-suspended to a concentration of 0.5% (volume/volume). the Tris-saline buffer consisted of 50 mM Trizma® hydrochloride/Trizma base and 100 mM sodium chloride, with a final pH of 7.0. Culture supernatants were serially diluted in Tris-saline buffer from 1:2 to 1:256. One hundred microliters of each dilution was added to nine hundred microliters of the rabbit red blood cells. Each dilution was set up in triplicate. The tubes were incubated for 30 minutes at 37° C. The samples were then centrifuged at 800×g for 6 minutes. Two two-hundred microliter aliquots were transferred to a microtiter plate and the optical density determined at 410 nm. Control fluids used in place of the culture supernatants included tris-saline buffer (zero lysis), 10% sodium dodecyl sulfate (100% lysis), and sterile growth medium containing the test compound. Units of activity are expressed as the reciprocal of the dilution of each test sample giving 50% lysis in samples that were adjusted to the same initial optical density (600 nm). As Table 7 below indicates terpineol significantly reduced the production of the alpha toxin.

TABLE 4

| Test Compound | % Test Compound | Hemolytic Endpoint 50% lysis | % Toxin Inhibition |
|---|---|---|---|
| None | 0 | 103 | N/A |
| Terpineol | 0.05% | 77 | 71% |
| Terpineol | 0.1% | 15 | 94% |

EXAMPLE 5

In this Example, the effect of terpineol in combination with the surface active agent Cetiol 1414E (myreth-3-myristate) was tested using a 4×4 checkerboard experimental design. This allowed the evaluation of the interaction of two test compounds on the growth of *S. aureus* and the production of TSST-1.

Four concentrations of terpineol (0.1%, 0.05%, 0.01%, and 0.0%) were combined with four concentrations of Cetiol 1414E (10 mM, 5 mM, 2.5 mM, and 0.0 mM) in a sixteen tube array. For example, tube #1 contained 0.0 mM Cetiol 1414E and 0.0% terpineol (vol/vol) in 10 mL of growth medium (as prepared in Example 1). Each of the tubes #1-#16 contained a unique combination of terpineol and Cetiol. The solutions were tested and evaluated as in Example 1. The effect of the test compounds on growth of *S. aureus* MN8 and on the production of TSST-1 is shown in Table 5 below.

TABLE 5

| Cetiol mM | Terpineol % | % CFU/ mL × $10^6$ | ng TSST-1 per mL | ngTSST-1 per CFU | % Reduction |
|---|---|---|---|---|---|
| 0 | 0 | 6.3 | 2008 | 319 | NA |
| 0 | 0.01 | 7.1 | 1650 | 234 | 27% |
| 0 | 0.05 | 6.6 | 906 | 137 | 57% |
| 0 | 0.1 | 5.7 | 249 | 44 | 86% |
| 2.5 | 0 | 4.2 | 1556 | 371 | 0% |
| 2.5 | 0.01 | 5.7 | 1130 | 117 | 38% |
| 2.5 | 0.05 | 5.1 | 800 | 157 | 51% |
| 2.5 | 0.1 | 2.6 | 146 | 57 | 82% |
| 5.0 | 0 | 5.9 | 1147 | 196 | 39% |
| 5.0 | 0.01 | 4.0 | 719 | 180 | 44% |
| 5.0 | 0.05 | 4.8 | 288 | 60 | 81% |
| 5.0 | 0.1 | 6.0 | 103 | 17 | 95% |
| 10.0 | 0 | 5.0 | 989 | 200 | 37% |
| 10.0 | 0.01 | 4.0 | 419 | 105 | 67% |
| 10.0 | 0.05 | 3.8 | 199 | 52 | 84% |
| 10.0 | 0.1 | 2.9 | 62 | 21 | 93% |

At every concentration of Cetiol 1414E, terpineol increased the inhibition of the production of TSST-1. The effect appears to be additive. Further, the addition of Cetiol 1414E increases the inhibition of TSST-1 production by terpineol.

In view of the above, it will be seen that the several objects of the invention are achieved. As various changes could be made in the above-described absorbent articles without departing from the scope of the invention, it is intended that all matter contained in the above description be interpreted as illustrative and not in a limiting sense.

What is claimed is:

1. An absorbent article comprising an effective amount of a first active ingredient comprising an isoprenoid compound effective in inhibiting the production of exoprotein from Gram positive bacteria by at least 40% and an effective amount of a second active ingredient comprising myreth-3-myristate, wherein the second active ingredient is effective in substantially inhibiting the production of exoprotein from Gram positive bacteria, and wherein the isoprenoid compound is present in an amount of from 0.5 micromoles per gram of absorbent article to 100 micromoles per gram of absorbent article, the first and second active ingredients being located on the outer surface of the absorbent article, and wherein the isoprenoid compound is selected from the group consisting of cis-terpin, trans-terpin, beta-terpinene, thujone, gamma-carotene, delta-carotene, lutein, and violaxanthin.

2. The absorbent article as set forth in claim 1 wherein the isoprenoid compound is present in an amount from about 1.0 micromoles per gram of absorbent article to about 50 micromoles per gram of absorbent article.

3. The absorbent article as set forth in claim 1 wherein the isoprenoid compound is effective in substantially inhibiting the production of TSST-1 from *S. aureus* bacteria.

4. The absorbent article as set forth in claim 1 wherein the isoprenoid compound is effective in substantially inhibiting the production of Enterotoxin B and alpha hemolysin from *S. aureus* bacteria.

5. The absorbent article as set forth in claim 1 wherein the absorbent article is selected from the group consisting of a catamenial tampon, a sanitary napkin, a panty liner, an incontinent undergarment, a diaper, a wound dressing, a dental tampon, a medical tampon, a surgical tampon and a nasal tampon.

6. The absorbent article as set forth in claim 1 wherein the isoprenoid compound reduces the formation of TSST-1 when the absorbent article is exposed to *S. aureus* by at least 40%.

7. The absorbent article as set forth in claim 1 wherein the isoprenoid compound reduces the formation of TSST-1 when the absorbent article is exposed to *S. aureus* by at least 50%.

8. The absorbent article as set forth in claim 1 wherein the isoprenoid compound reduces the formation of TSST-1 when the absorbent article is exposed to *S. aureus* by at least 60%.

9. The absorbent article as set forth in claim 1 wherein the isoprenoid compound reduces the formation of TSST-1 when the absorbent article is exposed to *S. aureus* by at least 70%.

10. The absorbent article as set forth in claim 1 wherein the isoprenoid compound reduces the formation of TSST-1 when the absorbent article is exposed to *S. aureus* by at least 80%.

11. The absorbent article as set forth in claim 1 wherein the isoprenoid compound reduces the formation of TSST-1 when the absorbent article is exposed to *S. aureus* by at least 90%.

12. The absorbent article as set forth in claim 1 wherein the isoprenoid compound reduces the formation of TSST-1 when the absorbent article is exposed to *S. aureus* by at least 95%.

13. The absorbent article as set forth in claim 1 further comprising a pharmaceutically active material selected from the group consisting of antimicrobials, antioxidants, anti-parasitic agents, antipruritics, astringents, local anaesthetics and anti-inflammatory agents.

14. The absorbent article as set forth in claim 1 further comprising an effective amount of a third active ingredient, said third active ingredient comprising a compound with an ether, ester, amide, glycosidic, or amine bond linking a $C_8$-$C_{18}$ fatty acid to an aliphatic alcohol wherein the third active ingredient is effective in substantially inhibiting the production of exoprotein from Gram positive bacteria.

15. The absorbent article as set forth in claim 1 wherein the absorbent article is a tampon and the isoprenoid compound is selected from the group consisting of cis-terpin, trans-terpin, and combinations thereof.

16. The absorbent article as set forth in claim 1 further comprising an effective amount of a third active ingredient, said third active ingredient comprising a compound with an ether, ester, amide, glycosidic, or amine bond linking a $C_8$-$C_{18}$ fatty acid to a polyalkoxylated sulfate salt wherein the third active ingredient is effective in substantially inhibiting the production of exoprotein from Gram positive bacteria.

17. The absorbent article as set forth in claim 1 further comprising an effective amount of a third active ingredient, said third active ingredient comprising a compound with an ether, ester, amide, glycosidic, or amine bond linking a $C_8$-$C_{18}$ fatty acid to a polyalkoxylated sulfosuccinic salt wherein the third active ingredient is effective in substantially inhibiting the production of exoprotein from Gram positive bacteria.

18. The absorbent article as set forth in claim 1 further comprising an effective amount of a third active ingredient having the general formula:

$$R^{10}—O—R^{11}$$

wherein $R^{10}$ is a straight or branched alkyl or straight or branched alkenyl having from 8 to about 18 carbon atoms and $R^{11}$ is selected from the group consisting of an alcohol, a polyalkoxylated sulfate salt and a polyalkoxylated sulfosuccinate salt wherein the third active ingredient is effective in substantially inhibiting the production of exoprotein from Gram positive bacteria.

19. The absorbent article as set forth in claim 18 wherein $R^{10}$ is a straight or branched alkyl group.

20. The absorbent article as set forth in claim 18 wherein $R^{10}$ is a straight or branched alkenyl group.

21. The absorbent article as set forth in claim 18 wherein $R^{10}$ is selected from the group consisting of caprylic acid, capric acid, lauric acid, myristic acid, palmitic acid and stearic acid.

22. The absorbent article as set forth in claim 18 wherein $R^{11}$ is an aliphatic alcohol.

23. The absorbent article as set forth in claim 22 wherein $R^{11}$ is an aliphatic alcohol selected from the group consisting of glycerol, glycol, sucrose, glucose, sorbitol, and sorbitan.

24. The absorbent article as set forth in claim 23 wherein $R^{11}$ is a glycol selected from the group consisting of ethylene glycol, propylene glycol, polypropylene glycol, and combinations thereof.

25. The absorbent article as set forth in claim 18 wherein the third active ingredient is selected from the group consisting of laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate and polyethylene oxide (2) sorbitol ether.

26. The absorbent article as set forth in claim 18 wherein the third active ingredient is present in an amount of at least about 0.0001 millimoles per gram of absorbent article.

27. The absorbent article as set forth in claim 18 wherein the third active ingredient is present in an amount of at least about 0.005 millimoles per gram of absorbent article.

28. The absorbent article as set forth in claim 18 wherein the third active ingredient is present in an amount from about 0.005 millimoles per gram of absorbent article to about 0.2 millimoles per gram of absorbent article.

29. The absorbent article as set forth in claim 18 wherein the third active ingredient is effective in substantially inhibiting the production of TSST-1 from *S. aureus* bacteria.

30. The absorbent article as set forth in claim 18 wherein the third active ingredient is effective in substantially inhibiting the production of Enterotoxin B from *S. aureus* bacteria.

31. The absorbent article as set forth in claim 18 wherein the absorbent article is selected from the group consisting of a catamenial tampon, a sanitary napkin, a panty liner, an incontinent undergarment, a diaper, a wound dressing, a dental tampon, a medical tampon, a surgical tampon and a nasal tampon.

32. The absorbent article as set forth in claim 18 wherein the combination of the first active ingredient, the second active ingredient, and the third active ingredient reduce the formation of TSST-1 when the absorbent article is exposed to *S. aureus* by at least about 80%.

33. The absorbent article as set forth in claim 18 wherein the combination of the first active ingredient, the second active ingredient, and the third active ingredient reduce the formation of TSST-1 when the absorbent article is exposed to *S. aureus* by at least about 90%.

34. The absorbent article as set forth in claim 18 wherein the combination of the first active ingredient, the second active ingredient, and the third active ingredient reduce the formation of TSST-1 when the absorbent article is exposed to *S. aureus* by at least about 95%.

35. The absorbent article as set forth in claim 18 further comprising a pharmaceutically active material selected from the group consisting of antimicrobials, antioxidants, antiparasitic agents, antipruritics, astringents, local anaesthetics and anti-inflammatory agents.

36. The absorbent article as set forth in claim 1 further comprising an effective amount of a third active ingredient, the third active ingredient comprising an alkyl polyglycoside effective in substantially inhibiting the production of exoprotein from Gram positive bacteria.

37. The absorbent article as set forth in claim 36 wherein the alkyl polyglycoside has an alkyl group having from about 8 to about 18 carbon atoms.

38. The absorbent article as set forth in claim 37 wherein the alkyl group is a linear alkyl group.

39. The absorbent article as set forth in claim 37 wherein the alkyl polyglycoside has an alkyl group having from about 8 to about 14 carbon atoms.

40. The absorbent article as set forth in claim 36 wherein the alkyl polyglycoside has an HLB of 12 to 14.

41. The absorbent article as set forth in claim 36 wherein the alkyl polyglycoside has an HLB of 10 to 15.

42. The absorbent article as set forth in claim 36 wherein the alkyl polyglycoside has the general formula:

$$H—(Z_n)—O—R^{14}$$

wherein Z is a saccharide residue having 5 or 6 carbon atoms, n is a whole number from 1 to 6, and $R^{14}$ is a linear alkyl group having from about 8 to about 18 carbon atoms.

43. The absorbent article as set forth in claim 42 wherein $R^{14}$ is a linear alkyl group having from about 8 to about 14 carbon atoms.

44. The absorbent article as set forth in claim 42 wherein $R^{14}$ is a linear alkyl group having from about 8 to about 12 carbon atoms.

45. The absorbent article as set forth in claim 42 wherein the absorbent article is selected from the group consisting of a catamenial tampon, a sanitary napkin, a panty liner, an incontinent garment, a diaper, a wound dressing, a dental tampon, a medical tampon, a surgical tampon, and a nasal tampon.

46. The absorbent article as set forth in claim 36 wherein the third active ingredient is present in an amount of at least about 0.0001 millimoles per gram of absorbent article.

47. The absorbent article as set forth in claim 36 wherein the third active ingredient is present in an amount of at least about 0.005 millimoles per gram of absorbent article.

48. The absorbent article as set forth in claim 36 wherein the third active ingredient is present in an amount of at least about 0.005 millimoles per gram of absorbent article to about 2 millimoles per gram of absorbent article.

49. The absorbent article as set forth in claim 36 wherein the combination of the first active ingredient, the second active ingredient, and the third active ingredient reduces the formation of TSST-1 when the absorbent article is exposed to *S. aureus* by at least about 80%.

50. The absorbent article as set forth in claim 36 wherein the combination of the first active ingredient, the second active ingredient, and the third active ingredient reduces the formation of TSST-1 when the absorbent article is exposed to *S. aureus* by at least about 90%.

51. The absorbent article as set forth in claim 36 wherein the combination of the first active ingredient, the second active ingredient, and the third active ingredient reduces the formation of TSST-1 when the absorbent article is exposed to *S. aureus* by at least about 95%.

52. The absorbent article as set forth in claim 1 further comprising an effective amount of a third active ingredient comprising glycerol monolaurate wherein said third active ingredient is effective in substantially inhibiting the production of exoprotein from Gram positive bacteria.

53. The absorbent article as set forth in claim 1 further comprising an effective amount of a third active ingredient having the general formula:

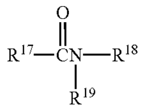

wherein $R^{17}$, inclusive of the carbonyl carbon, is an alkyl group having 8 to 18 carbon atoms, and $R^{18}$ and $R^{19}$ are independently selected from hydrogen or an alkyl group having from 1 to about 12 carbon atoms which may or may not be substituted with groups selected from ester groups, ether groups, amine groups, hydroxyl groups, carboxyl groups, carboxyl salts, sulfonate groups, sulfonate salts, and mixtures thereof wherein said third active ingredient is effective in substantially inhibiting the production of exoprotein from Gram positive bacteria.

54. The absorbent article as set forth in claim 53 wherein $R^{17}$ is derived from a saturated or unsaturated fatty acid.

55. The absorbent article as set forth in claim 54 wherein $R^{17}$ is derived from an acid selected from the group consisting of caprylic acid, capric acid, lauric acid, myristic acid, palmitic acid, and stearic acid.

56. The absorbent article as set forth in claim 53 wherein the third active ingredient is selected from the group consisting of sodium lauryl sarcosinate, lauramide monoethanolamide, lauramide diethanolamide, lauramidopropyl dimethylamine, disodium lauramide monoethanolamide sulfosuccinate, and disodium lauroamphodiacetate.

57. The absorbent article as set forth in claim 53 wherein the third active ingredient is present in an amount of at least about 0.0001 millimoles per gram of absorbent article.

58. The absorbent article as set forth in claim 53 wherein the third active ingredient is present in an amount of at least about 0.0005 millimoles per gram of absorbent article.

59. The absorbent article as set forth in claim 53 wherein the third active ingredient is present in an amount from about 0.005 millimoles per gram of absorbent article to about 0.2 millimoles per gram of absorbent article.

60. The absorbent article as set forth in claim 53 wherein the third active ingredient is effective in substantially inhibiting the production of TSST-1 from *S. aureus* bacteria.

61. The absorbent article as set forth in claim 53 wherein the third active ingredient is effective in substantially inhibiting the production of Enterotoxin B from *S. aureus* bacteria.

62. The absorbent article as set forth in claim 53 wherein the absorbent article is selected from the group consisting of a catamenial tampon, a sanitary napkin, a panty liner, an incontinent undergarment, a diaper, a wound dressing, a dental tampon, a medical tampon, a surgical tampon and a nasal tampon.

63. The absorbent article as set forth in claim 53 wherein the combination of the first active ingredient, the second active ingredient, and the third active ingredient reduce the formation of TSST-1 when the absorbent article is exposed to *S. aureus* by at least about 80%.

64. The absorbent article as set forth in claim 53 wherein the combination of the first active ingredient, the second active ingredient, and the third active ingredient reduce the formation of TSST-1 when the absorbent article is exposed to *S. aureus* by at least about 90%.

65. The absorbent article as set forth in claim 53 wherein the combination of the first active ingredient, the second active ingredient, and the third active ingredient reduce the formation of TSST-1 when the absorbent article is exposed to *S. aureus* by at least about 95%.

66. The absorbent article as set forth in claim 53 further comprising a pharmaceutically active material selected from the group consisting of antimicrobials, antioxidants, anti-parasitic agents, antipruritics, astringents, local anaesthetics and anti-inflammatory agents.

67. The absorbent article as set forth in claim 1 further comprising an effective amount of a third active ingredient having the general formula:

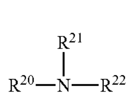

wherein $R^{20}$ is an alkyl group having from about 8 to about 18 carbon atoms and $R^{22}$ and $R^{22}$ are independently selected from the group consisting of hydrogen and alkyl groups having from 1 to about 18 carbon atoms and which can have one or more substitutional moieties selected from the group consisting of hydroxyl, carboxyl, carboxyl salts and imidazoline wherein the third active ingredient is effective in substantially inhibiting the production of exoprotein from Gram positive bacteria.

68. The absorbent article as set forth in claim 67 wherein $R^{22}$ comprises a carboxyl salt, the carboxyl salt having a cationic moiety selected from the group consisting of sodium, potassium and combinations thereof.

69. The absorbent article as set forth in claim 67 wherein $R^{22}$ comprises an amine selected from the group consisting of lauramine, lauramino, propionic acid, sodium laurimino-dipropionic acid, lauryl hydroxyethyl imidazoline and mixtures thereof.

70. The absorbent article as set forth in claim 67 wherein the third active ingredient is present in an amount of at least about 0.0001 millimoles per gram of absorbent article.

71. The absorbent article as set forth in claim 67 wherein the third active ingredient is present in an amount of at least about 0.005 millimoles per gram of absorbent article.

72. The absorbent article as set forth in claim 67 wherein the third active ingredient is present in an amount from about 0.005 millimoles per gram of absorbent article to about 0.2 millimoles per gram of absorbent article.

73. The absorbent article as set forth in claim 67 wherein the absorbent article is selected from the group consisting of a catamenial tampon, a sanitary napkin, a panty liner, an incontinent undergarment, a diaper, a wound dressing, a dental tampon, a medical tampon, a surgical tampon and a nasal tampon.

74. The absorbent article as set forth in claim 67 wherein the combination of the first active ingredient, the second active ingredient, and the third active ingredient reduce the formation of TSST-1 when the absorbent article is exposed to *S. aureus* by at least about 80%.

75. The absorbent article as set forth in claim 67 wherein the combination of the first active ingredient, the second active ingredient, and the third active ingredient reduce the formation of TSST-1 when the absorbent article is exposed to *S. aureus* by at least about 90%.

76. The absorbent article as set forth in claim 67 wherein the combination of the first active ingredient, the second active ingredient, and the third active ingredient reduce the formation of TSST-1 when the absorbent article is exposed to *S. aureus* by at least about 95%.

77. The absorbent article as set forth in claim 67 further comprising a pharmaceutically active material selected from the group consisting of antimicrobials, antioxidants, anti-parasitic agents, antipruritics, astringents, local anaesthetics and anti-inflammatory agents.

78. The absorbent article as set forth in claim 1 further comprising an effective amount of a third active ingredient having the general formula:

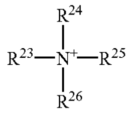

wherein $R^{23}$ is an alkyl group having from 8 to about 18 carbon atoms and $R^{24}$, $R^{25}$, and $R^{26}$ are independently selected from the group consisting of hydrogen and alkyl group having from 1 to about 18 carbon atoms and which can have one or more substitutional moieties selected from the group consisting of hydroxyl, carboxyl, carboxyl salts, and imidazoline wherein the third active ingredient is effective in substantially inhibiting the production of exoprotein from Gram positive bacteria.

79. The absorbent article as set forth in claim 78 wherein the third active ingredient is triethanolamide laureth sulfate.

80. The absorbent article as set forth in claim 78 wherein the third active ingredient is present in an amount of at least about 0.0001 millimoles per gram of absorbent article.

81. The absorbent article as set forth in claim 78 wherein the third active ingredient is present in an amount of at least about 0.005 millimoles per gram of absorbent article.

82. The absorbent article as set forth in claim 78 wherein the third active ingredient is present in an amount from about 0.005 millimoles per gram of absorbent article to about 0.2 millimoles per gram of absorbent article.

83. The absorbent article as set forth in claim 78 wherein the third active ingredient is effective in substantially inhibiting the production of TSST-1 from *S. aureus* bacteria.

84. The absorbent article as set forth in claim 78 wherein the third active ingredient is effective in substantially inhibiting the production of Enterotoxin B from *S. aureus* bacteria.

85. The absorbent article as set forth in claim 78 wherein the absorbent article is selected from the group consisting of a catamenial tampon, a sanitary napkin, a panty liner, an incontinent undergarment, a diaper, a wound dressing, a dental tampon, a medical tampon, a surgical tampon and a nasal tampon.

86. The absorbent article as set forth in claim 78 wherein the combination of the first active ingredient, the second active ingredient, and the third active ingredient reduce the formation of TSST-1 when the absorbent article is exposed to *S. aureus* by at least about 80%.

87. The absorbent article as set forth in claim 78 wherein the combination of the first active ingredient, the second active ingredient, and the third active ingredient reduce the formation of TSST-1 when the absorbent article is exposed to *S. aureus* by at least about 90%.

88. The absorbent article as set forth in claim 78 wherein the combination of the first active ingredient, the second active ingredient, and the third active ingredient reduce the formation of TSST-1 when the absorbent article is exposed to *S. aureus* by at least about 95%.

89. The absorbent article as set forth in claim 78 further comprising a pharmaceutically active material selected from the group consisting of antimicrobials, antioxidants, antiparasitic agents, antipruritics, astringents, local anaesthetics and anti-inflammatory agents.

90. The absorbent article as set forth in claim 1 wherein the second active ingredient is present in an amount of from about 2.5 mM per gram of absorbent article to about 10.0 mM per gram of absorbent article.

91. The absorbent article as set forth in claim 90 wherein the second active ingredient is present in an amount of from about 5.0 mM per gram of absorbent article to about 10.0 mM per gram of absorbent article.

92. The absorbent article as set forth in claim 91 wherein the second active ingredient is present in an amount of 10.0 mM per gram of absorbent article.

* * * * *

UNITED STATES PATENT AND TRADEMARK OFFICE

CERTIFICATE OF CORRECTION

PATENT NO. : 8,084,046 B2
APPLICATION NO. : 09/969199
DATED : December 27, 2011
INVENTOR(S) : Rae E. Syverson et al.

It is certified that error appears in the above-identified patent and that said Letters Patent is hereby corrected as shown below:

In the Specification

In TABLE 5, Column 16, Line 47, delete "mL × $10^6$" and insert -- mL × $10^8$ -- therefor.

In the Claims

In Claim 67, Column 21, line 56, delete "$R^{22}$ and $R^{22}$" and insert -- $R^{21}$ and $R^{22}$ -- therefor.

Signed and Sealed this
Twelfth Day of May, 2015

Michelle K. Lee
*Director of the United States Patent and Trademark Office*